United States Patent [19]

Post et al.

[11] Patent Number: 4,694,249
[45] Date of Patent: Sep. 15, 1987

[54] METHOD FOR RECORDING THE NUCLEAR MAGNETIC RESONANCE FOR USE IN VNMR TOMOGRAPHY

[75] Inventors: Hans Post, Schriesheim; Dieter Ratzel, Rheinstetten; Peter Brunner, Ettlingen; Bertold Knüttel, Rheinstetten-Moersch, all of Fed. Rep. of Germany

[73] Assignee: Bruker Medizintechnik G.m.b.H., Fed. Rep. of Germany

[21] Appl. No.: 815,118

[22] Filed: Dec. 27, 1985

Related U.S. Application Data

[63] Continuation of Ser. No. 474,698, Mar. 11, 1983, abandoned.

[30] Foreign Application Priority Data

Mar. 18, 1982 [DE] Fed. Rep. of Germany ....... 3209810

[51] Int. Cl.$^4$ ............................................ G01R 33/20
[52] U.S. Cl. ..................................................... 324/309
[58] Field of Search ............... 324/300, 307, 309, 312, 324/314

[56] References Cited

U.S. PATENT DOCUMENTS

| | | | |
|---|---|---|---|
| 4,115,730 | 9/1978 | Mansfield | 324/309 |
| 4,297,637 | 10/1981 | Crooks et al. | 324/309 |
| 4,318,043 | 3/1982 | Crooks et al. | 324/309 |
| 4,471,305 | 9/1984 | Crooks et al. | 324/309 |
| 4,486,708 | 12/1984 | Macovski | 324/309 |

OTHER PUBLICATIONS

J. M. S. Hutchison et al., J. Phys. E: Sci. Instrum. vol. 13, pp. 947-955 (1980).
W. A. Edelstein et al., Physics in Medicine and Biology, vol. 25, pp. 751-756 (1980).
G. Johnson et al., J. Phys. E. Sci. Instrum. vol. 15, pp. 74-79 (1982).

*Primary Examiner*—Michael J. Tokar
*Attorney, Agent, or Firm*—Pennie & Edmonds

[57] ABSTRACT

For recording the nuclear magnetic resonance in selected areas of a body for the purpose of representing body cross-sections in the form of images (NMR tomography), wherein the nuclear spins of a selected type present in the area of one plane of the body are subjected to a superimposed gradient field varying in the selected cross-sectional plane, and selectively excited, the excitation of the nuclear spins is effected by application of a pulse sequence which induces the nuclear spins to supply at one stage a number of chronologically successive induction signals. The induction signals corresponding to each other in chronolical sequence are then processed to obtain separate sets of image signals so that by one single measurement a sequence of cross-sectional images is obtained which differ from each other by the intensity of the excited nuclear spins which varies according to the relaxation times $T_1$ or $T_2$. The fact that all images have been obtained by one and the same measurement provides the possibility to determine the relaxation times $T_1$ and/or $T_2$ related to the individual image points and to use them on the one hand for purposes of selective image representation and, on the other hand, for improving the image quality.

15 Claims, 10 Drawing Figures

METHOD FOR RECORDING THE NUCLEAR MAGNETIC RESONANCE FOR USE IN VNMR TOMOGRAPHY

This is a continuation of application Ser. No. 474,698, filed Mar. 11, 1983, now abandoned.

BACKGROUND OF THE INVENTION

The present invention relates to a method for recording the nuclear magnetic resonance in selected areas of a body for the purpose of representing body cross-sections in the form of images (NMR tomography), in which the nuclear spins of a selected type present in the area of one plane of the body are subjected to a superimposed gradient field varying in the selected cross-sectional plane, and selectively excited, whereupon the induction signals supplied by the excited nuclear spins are processed by calculation to obtain image signals.

The cross-sectional images obtained by NMR tomography represent substantially the density distribution of the nuclear spins of the selective type in the cross-sectional plane. But the signal amplitude responsible for the light intensity of the individual image points depends not only on the density of the excited nuclear spins, but also on their state of excitation. Further, the image quality is affected to a quite considerable degree by unavoidable noise signals. There are, consequently, considerable elements of uncertainty in the information content of images of body cross-sections obtained by NMR tomography, and the images obtained are not of the desirable quality.

Accordingly, it is an object of the present invention to improve the known methods used in NMR tomography to increase the information content and the quality of the images obtained.

SUMMARY OF THE INVENTION

According to the present invention, this object is achieved by a method characterized in that the excitation of the nuclear spins is achieved in the conventional manner by means of a pulse sequence which induces the nuclear spins to produce at each stage a number of chronological induction signals, and that the induction signals corresponding to each other in chronological sequence are processed into separate sets of image signals so that a single meansurement provides a sequence of cross-sectional images differing from each other by the intensity of the excited core spins which vary according to the spin-lattice and spin-spin relaxation times $T_1$ and $T_2$ respectively.

By using the method of the invention, one obtains by a single measurement not only the one image usual heretofore, but a number of images of considerably different structures because the excited core spins found in different structures of the body cross-section have different relaxation times $T_1$ and $T_2$ so that the signal intensity of the individual structures of the body cross-section varies during the recording time. In the course of such variations, certain details of the chronologically successive images may vanish and be replaced by others which could not be seen before. The particular advantage of the method of the invention is to be seen in the fact that one has not to pay for the additional information thus gained with a notable extention of the measuring time which could not be tolerated in particular in medical applications and which in the case of in vivo measurements could quite generally lead to changes in the position of the object under examination and, thus, a considerable loss of information. Contrary to image sequences that could be obtained by several repeated measurements, the images obtained by the method of the invention distinguish themselves by absolute coincidence.

DETAILED DESCRIPTION

Figure 1A:
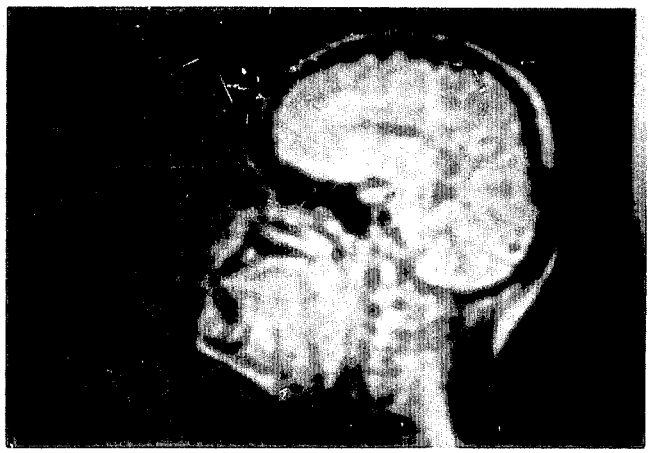
FIGS. 1a, 1b, 1c, 1d and 1e are photographs taken using the method of the present invention showing tomographic images of a sagittal cross-sectional plane through a human head with FIG. 1a being a first image obtained, 16 ms following a first excitaton and FIGS. 1b, 2c, 3d and 4e showing images obtained at 32 ms intervals thereafter.
Figure 1B:
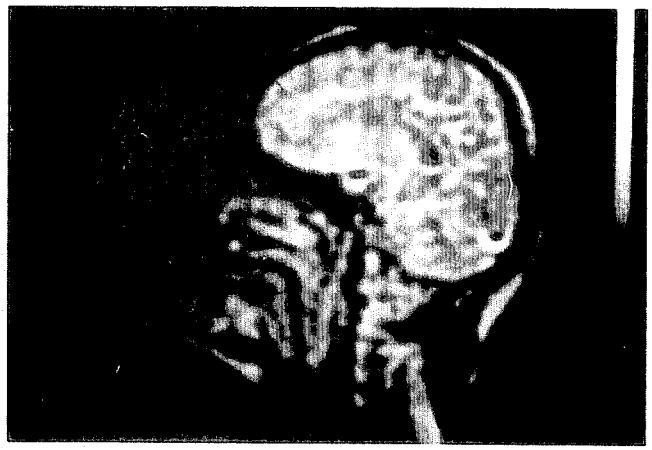
Figure 1C:
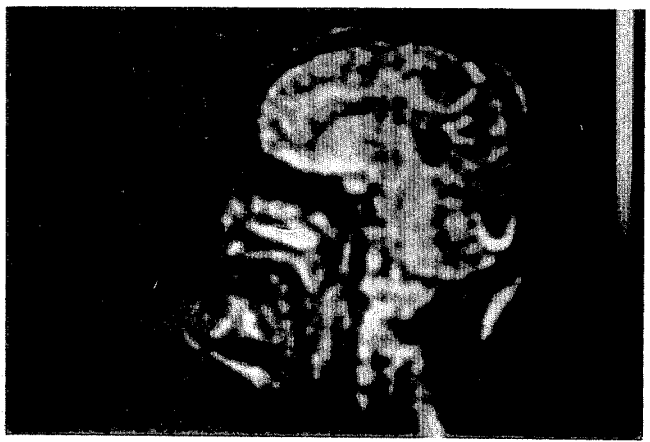
Figure 1D:
Figure 1E:
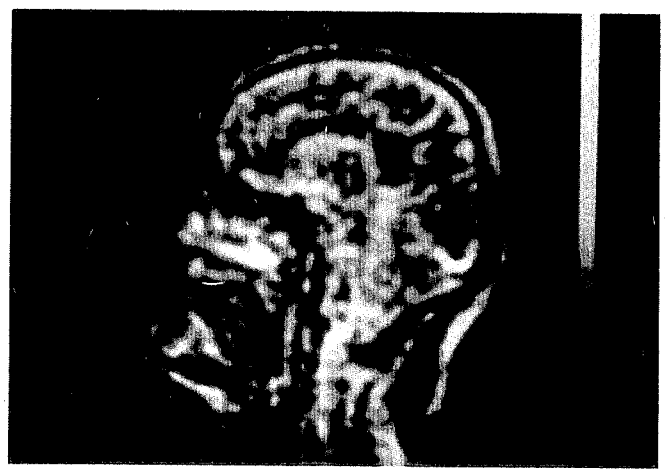

The pulse sequences used in the method of the invention may be the same as those used in normal NMR spectography for determining the relaxation times. These are in the case of $T_1$ in particular the DEFT sequence (see E. D. Becker et al in J. Amer. Chem. Soc., vol. 91 (1969), p.7784) or corresponding variangs thereof, and in the case of $T_2$ a Carr-Purcell sequence with or without Gill-Meiboom modification. But while in classical NMR spectography the signals are intregrally derived from the whole sample volume and, therefore, directly comparable, the successive interferograms excited by such a pulse sequence do not lend themselves for such a comparison because the individual interferograms represent the signals from large volume domains which do not supply directly usable data. Rather, comprehensive processing of the free induction signals is required to obtain the desired information on the individual image points. So, the only measure that suggested itself was to add up the induction signals obtained by such a pulse sequence in the conventional manner, prior to processing them further, in order to improve the signal-to-noise ratio. However, the improvement of the image quality thus obtainable is not nearly as great as that achievable by the method of the invention. In addition, it is a disadvantage of the above method that the information relating to the relaxation times get lost, whereas in the method of the invention this information is gained by the step of processing the individual induction signals corresponding to each other in chronological sequence into separate sets of image signals.

As mentioned before, it is a particular advantage of the method of the invention that all images representing chronologically successive states are gained by one and the same measurement so that they provide absolute conicidence and an exact comparison. This then offers the possibility to relate the image signals associated with the individual image points to each other and to derive from the variation of the image signals associated with the individual image points the relaxation times $T_1$ and-/or $T_2$ for the individual volume elements of the body cross-section related to the respective image points. Considering that the method of the invention can supply a relatively large number, for instance 24, of chronological parameters for each image point, it is possible to derive therefrom the e-functions characteristic of the relaxation times $T_1$ and/or $T_2$ with great accuracy. The same degree of accuracy is achieved in determining the relaxation times related to the individual image points. Since it has been found that the relaxation times $T_1$ and $T_2$ of excited nuclear spins in cancer tissue are considerably greater than those of nuclear spins in similar sound tissue, the exact determination of the relaxation times $T_1$ and $T_2$ is of considerable importance. The fact that the method of the invention offers the possibility to derive from the images obtained different relaxation times should open up interesting perspectives for cancer diagnosis as it is no longer necessary to carry out separate in vitro examinations of individual tissue samples.

The fact that the method of the invention permits to determine the relaxation times $T_1$ and $T_2$ for the individual volume elements of the body cross-section with great accuracy opens up the possibility to produce, by way of a further improvement of the invention, a set of image signals represeting only the density of nuclear spins having a selected relaxation time $T_1$ or $T_2$.

If, for instance, the spin-spin relaxation time $T_2$ of a typical cancer tissue were known, there would be the possibility to produce with the method of the invention images representing exclusively those body areas which contain cancer tissue. So, one could for instance determine the relaxation time $T_2$ of cancer tissue removed in the course of an operation and examine the patient later with the aid of the method of the invention to determine if tissue presenting the same relaxation time $T_2$ develops again in his body, and in particular in the neighbourhood of the operation site.

The fact that due to the exact coincidence of the individual points of the image set obtained the relaxation times $T_1$ and $T_2$ related to the individual image points can be determined with great accuracy opens up an experimental way to correct all image points of the individual images so as to bring their intensity exactly to the value which it must have according to the e-function obtained from the determined relaxation time. In this manner, any disturbance by noise signals and the like can be considerably reduced so that it is possible, without any extension of the measuring time, to obtain images of a quality which is necessarily better than that achievable by the usual methods forimproving the signal-to-noise ratio.

It is a precondition of the method of the invention that the nuclear spins to be excited by means of the pulse sequence in the area of the selected body plane have not been previously subjected to influence which disturbed their orientation relative to the homogeneous static magnetic field so that when a pulse sequence consisting of 90° and 180° pulses is applied, their orientation in parallel to the static magnetic field is constantly restored so that they can supply a plurality of successive induction signals. In the simplest of all cases, the method can be used for examining a body which exhibits from the very beginning the shape of a disk, whose entire volume supplies the image to be produced and which, accordingly, need not be subjected to any particular steps for preparing a particular cross-sectional plane for the image-forming process. The method of the invention is also of definite interest for examinations of organic and anorganic bodies which can without any problems be cut mechanically into disks suited for producing NMR images which give the desired information on the structure of the bodies.

But there definitely also exists the possibility to prepare a body by special excitation steps to ensure that only the nuclear spins obtained in the selected body plane are oriented in parallel to the static magnetic field and, thus, available for an excitation supplying a defined signal. In a further improvement of the invention, the selection of the body plane is, therefore, effected by application of a gradient field extending in parallel to the homogeneous magnetic field and varying in a direction perpendicular to the selected plane, and selected pulse signals which provide both, a selective excitation of the nuclear spins of the selected type contained in the selected plane and an excitation of the entirety of the selected nuclear spins in a manner such that only the nuclear spins contained in the selected plane resume the orientation in the sense of the static magnetic field. An excitation method of this type is the subject-matter of a prior U.S. patent application Ser. No. 474,699 which describes the method in detail so that this description need not be repeated here.

Figure 2A:
FIGS. 2a, 2b, 2c, 2d and 2e are photographs taken using the method of the present invention showing tomographic images of a transverse cross-sectional plane through a human head with FIG. 2a being a first image obtained 16 ms following a first excitation and FIGS. 2b, 2c, 2d and 2e showing images obtained at 32 ms intervals thereafter.
Figure 2B:
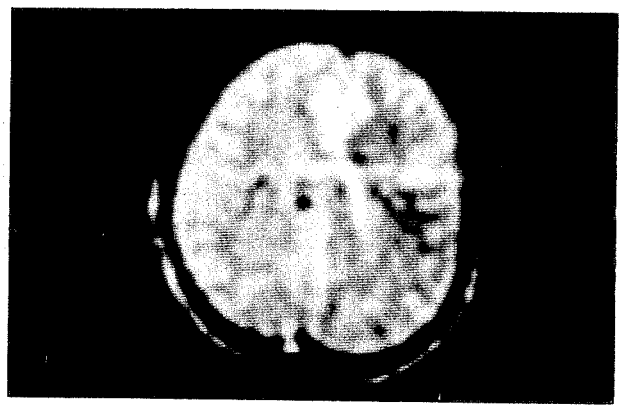
Figure 2C:
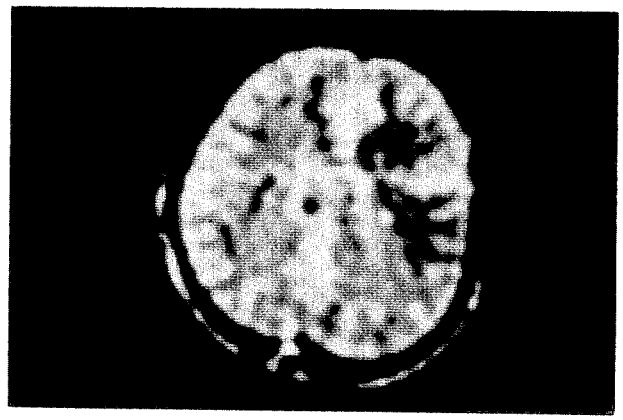
Figure 2D:
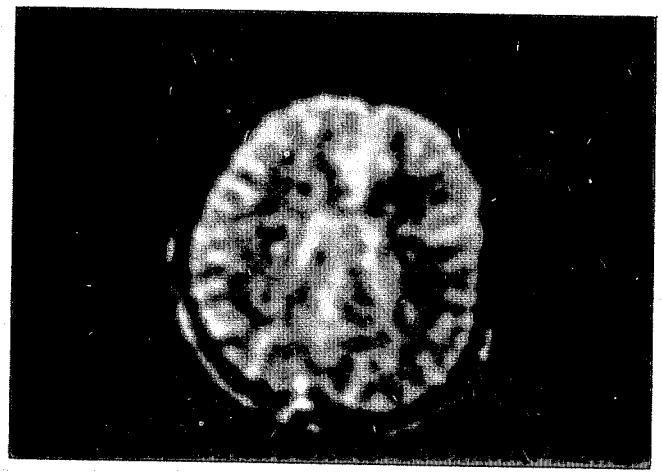
Figure 2E:
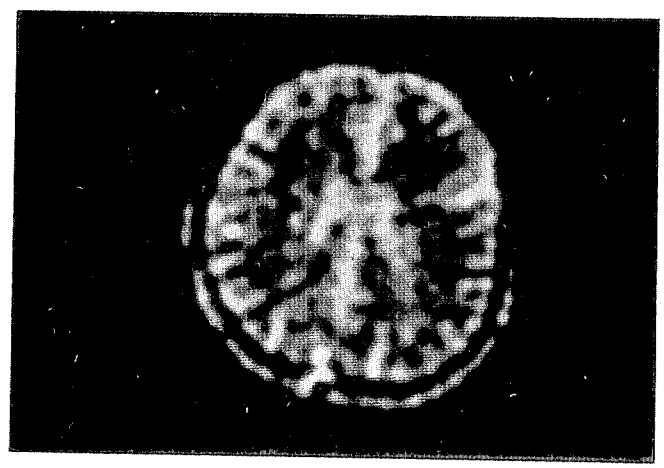

To demonstrate the value and importance of the method of the invention, two sets of photographs are attached which represent a sequence of cross-sectional images obtained by the method of the invention. The photographs show tomographic images of a sagittal (FIGS. 1a, 2b, 3c, 4d, 5e) and a transverse (FIGS. 2a, 2b; 2c, 2d, 2e) cross-sectional plane through a human head. The selection of the cross-sectional planes was effected with the aid of the method described by the patient application just mentioned. The exitation of the selected spins of protons was achieved by applying a Carr-Purcell sequence in such a manner that the first image was obtained 16 ms following the first excitation, and the other images at intervals of 32 ms each thereafter. The differences in structure of the successive images are striking. Structures clearly visible in the first image vanish gradually and give room to other structures. One will note, for instance, that a small light circular bow develops in the lower section of the back of the head in the sagittal images whereas a large dark bow to be seen a little lower vanishes gradually. Similarly, the central structure of the transverse cross-sectional image changes considerably. In both series of images. The image of the brain substance is gradually superseded by the image of the brain structure.

It should be noted that the attached photos have by no means the quality that can be achieved with the method of the invention. This is due to the fact that on the one hand each image has been obtained by summing up four successive images and, on the other hand, the before-described correction by means of the determined $T_2$ values has not carried out yet.

We claim:

1. A nuclear-magnetic-resonance tomographic method for producing a sequence of images derived from an ensemble of nuclear spins within a preselected cross-sectional plane passing through a body, each image being associated with a particular time and representing a two-dimensional distribution of nuclear-spin polarization of the ensemble of nuclear spins in the plane, different images representing different two-dimensional distributions of nuclear-spin polarization from the same ensemble of nuclear spins as a result of different degrees of spin relaxation of the polarization at different locations within the cross-sectional plane at the diffferent times of the images, the method comprising the steps of:

(a) subjecting at least a portion of the body which includes the preselected cross-sectional plane to a polarizing magnetic field to polarize the nuclear spins in the plane, the polarizing magnetic field being essentially static and effectively homogeneous in the cross-sectional plane;

(b) superimposing upon said polarizing magnetic field in the cross-sectional plane at least one magnetic-resonance-tomographic-imaging magnetic gradient field produced in accordance with a magnetic-resonance-tomographic-image generation process, each magnetic gradient field having a field component directed essentially parallel to the polarizing magnetic field, the magnetic-resonance-tomographic-imaging magnetic gradient fields varying in magnitude along directions relative to the preselected cross-sectional plane effective to permit nuclear-magnetic-resonance signals to be tomographically detected from nuclear spins located in the plane in accordance with the magnetic-resonance-tomographic-image generation process;

(c) exciting nuclear spins in the cross-sectional plane with a spin-echo-inducing pulse sequence of radio-frequency pulses, the pulse sequence having a first pulse and causing the excited nuclear spins to produce a sequence of spin-echo nuclear-magnetic-resonance signals in a timed relation relative to pulses in the pulse sequence, each spin-echo signal occurring at a time after the first pulse of the pulse sequence which defines a spin-echo-occurance time characteristic of the particular spin-echo signal, each spin-echo signal being representative of a distribution of nuclear-spin polarization resulting from the ensemble of nuclear spins in the cross-sectional plane under the influence of the polarizing magnetic field and the magnetic gradient fields with the nuclear spins at each different location within the plane at the degree of spin relaxation characteristic of the location at the spin-echo-occurance time of the spin-echo signal;

(d) repeating steps (b) and (c) a tomographic-image-generation number of times less one, at least one magnetic-resonance-tomographic-imaging magnetic gradient field being altered with each repetition of step (b) in accordance with the magnetic-resonance-tomographic-image generation process, each repetition of steps (b) and (c) producing a sequence of spin-echo nuclear magnetic-resonance signals, each spin-echo signal in the sequence being characterized by one of the spin-echo occurance times;

(e) digitizing at least a portion of each spin-echo signal; and (f) for each spin-echo occurance time, combining the digitized spin-echo signals associated with the particular spin-echo occurance time produced by the tomographic-image generation number of spin-echo-inducing pulse sequences to form a magnetic-resonance-tomographic-image in accordance with the magnetic-resonance-tomographic-image generation process, each image being characterized by the spin-echo occurance time of the digitized spin-echo signals combined to form the image and representing the two-dimensional distribution of nuclear-spin polarization resulting from the ensemble of nuclear spins in the cross-sectional plane and reflecting the different degrees of spin relaxation at different locations of the nuclear spins within the plane at the spin-echo occurance time.

2. The nuclear-magnetic-resonance-tomographic method in accordance with claim 1 wherein each sequence of spin-echo signals corresponding to a pulse sequence is digitized and stored before spin-echo signals corresponding to identical spin-echo occurance times in said sequences are combined.

3. The nuclear-magnetic-resonance-tomographic method in accordance with claim 1 wherein the spin-echo-inducing pulse sequences are selected to cause the spin-echo signals forming a sequence to vary substantially in accordance with spin-spin relaxation times of the ensemble of nuclear spins at different locations in the cross-sectional plane.

4. The nuclear-magnetic-resonance-tomographic method in accordance with claim 3 wherein each of the spin-echo-inducing pulse sequences is of a Carr-Purcell sequence type.

5. The nuclear-magnetic-resonance-tomographic method in accordance with claim 3 wherein a sufficient number of images are produced to determine e-functions characteristic of the spin-spin relaxation times of the nuclear spins at a plurality of different locations in the cross-sectional plane.

6. The nuclear-magnetic-resonance-tomographic method in accordance with claim 5 wherein for each location in the cross-sectional plane represented by the sequence of images an e-function is determined having a spin-spin relaxation time characteristic of the location.

7. The nuclear-magnetic-resonance-tomographic method in accordance with claim 5 wherein the intensity of individual locations represented in an image are corrected in accordance with e-functions determined to correspond to the locations.

8. The nuclear-magnetic-resonance-tomographic method in accordance with claim 1 wherein the spin-echo signals forming a sequence to vary substantially in accordance with the spin-lattice relaxation times of the ensemble of nuclear spins at different locations in the cross-sectional plane.

9. The nuclear-magnetic-resonance-tomographic method in accordance with claim 8 wherein each of the spin-echo-inducing pulse sequences is of a DEFT-sequence type.

10. The nuclear-magnetic-resonance-tomographic method in accordance with claim 8 wherein a sufficient number of images are produced to determine e-functions characteristic of the spin-lattice relaxaton times of the nuclear spins at a plurality of different locations in the cross-sectional plane.

11. The nuclear-magnetic-resonance-tomographic method in accordance with claim 10 wherein for each location in the cross-sectional plane represented by a sequence of images an e-function is determined having a spin-lattice relaxation time characteristic of the location.

12. The nuclear-magnetic-resonance-tomographic method in accordance with claim 10 wherein the intensity of individual locations represented in an image are corrected in accordance with e-functions determined to correspond to the locations.

13. The nuclear-magnetic-resonance-tomographic method according to claim 1 wherein the body has a thin essentially planar shape and the preselected cross-sectional plane passing through the body constitutes essentially the entire body so that nuclear-magneticresonance signals are tomographically detected from nuclear spins from essentially the entire body.

14. The nuclear-magnetic-resonance-tomographic method according to claim 1 wherein the body has an extended shape in a direction perpendicular to the preselected cross-sectional plane passing through the body and the step of superimposing at least one magnetic-resonance-tomographic-imaging magnetic gradient field upon the polarizing magnetic field includes imposing a slice-selection magnetic gradient field upon the polarizing field, the slice-selection magnetic gradient field having a field component directed essentially parallel to the polarizing magnetic field, said component being substantially constant in magnitude over the cross-sectional plane and varying in magnitude along a direction perpendicular to the cross-sectional plane to permit nuclear-magnetic-resonance signals to be tomographically detected from nuclear spins located in the plane in accordance with the magnetic-resonance-tomographic-image generation process.

15. A nuclear-magnetic-resonance tomographic method for producng a sequence of images derived from an ensemble of nuclear spins within a preselected cross-sectional plane passing through a body, each image being associated with a particular time and representing a two-dimensional distribution of nuclear-spin polarization of the ensemble of nuclear spins in the plane, different images representing different two-dimensional distributions of nuclear-spin polarization from the same ensemble of nuclear spins as a result of different degrees of spin relaxation of the polarization at different locations within the cross-sectional plane at the different times of the images, the method comprising the steps of:

(a) subjecting at least a portion of the body which includes the preselected cross-sectional plane to a polarizing magnetic field to polarize the nuclear spins in the plane, the polarizing magnetic field being essentially static and effectively homogenous in the cross-sectional plane;

(b) superimposing upon said polarizing magnetic field in the cross-sectional plane at least one magnetic-resonance-tomographic-imaging magnetic gradient field produced in accordance with a magnetic-resonance-tomographic-image generation process, each magnetic gradient field having a field component directed essentially parallel to the polarizing magnetic field, the magnetic-resonance-tomographic-imaging magnetic gradient fields varying in magnitude along directions relative to the preselected cross-sectional plane effective to permit nuclear-magnetic-resonance signals to be tomographically detected from nuclear spins located in the plane in accordance with the magnetic-resonance-tomographic-image generation process;

(c) exciting nuclear spins in the cross-sectional plane with a spin-echo-inducing pulse sequence of radio-frequency pulses, the pulse sequence having a first pulse and causing the excited nuclear spins to produce a sequence of spin-echo nuclear-magnetic-resonance signals in a timed relation relative to pulses in the pulse sequence, each spin-echo signal occurring at a time after the first pulse of the pulse sequence which defines a spin-echo-occurance time characteristic of the particular spin-echo signal, each spin-echo signal being representive of a distribution of nuclear-spin polarization resulting from the ensemble of nuclear spins in the cross-sectional plane under the influence of the polarizing magnetic field and the magnetic gradient fields with the nuclear spins at each different location within the plane at the degree of spin relaxation characteristic of the location at the spin-echo-occurance time of the spin-echo signal;

(d) digitizing and storing at least a portion of each spin-echo signal;

(e) repeating steps (b), (c) and (d) a tomographic-image-generation number of times less one, at least one magnetic-resonance-tomographic-imaging magnetic gradient field being altered with each repetition of step (b) in accordance with the magnetic-resonance-tomographic-image generation process, each repetition of steps (b), (c) and (d) producing a stored sequence of digitized spin-echo nuclear-magnetic-resonance signals, each digitized spin-echo signal in the sequence being characterized by one of the spin-echo-occurance times;

(f) after all of the spin-echo signal portions have been digitized and stored, combining for each spin-echo occurance time the digitized spin-echo signals associated with the particular spin-echo occurance time produced by the tomographic-image generation number of spin-echo-inducing pulse sequences to form a magnetic-resonance-tomographic-image in accordance with the magnetic-resonance-tomographic-image generation process, each image being characterized by the spin-echo occurance time of the digitized spin-echo signals combined to form the image and representing the two-dimensional distribution of nuclear-spin polarization resulting from the ensemble of nuclear spins in the cross-sectional plane and reflecting the different degrees of spin relaxation at different locations of the nuclear spins within the plane at the spin-echo occurance time.

* * * * *